United States Patent [19]
O'Keeffe

[11] Patent Number: 5,866,804
[45] Date of Patent: Feb. 2, 1999

[54] DEVICE AND METHOD FOR MEASURING, MONITORING, AND CONTROLLING FAT AND MICELL ASSOCIATED PROTEIN CONCENTRATION IN STANDARDIZED MILK

[76] Inventor: Michael G. O'Keeffe, P.O. Box 541, Hopewell Junction, N.Y. 12533

[21] Appl. No.: 735,663

[22] Filed: Oct. 24, 1996

Related U.S. Application Data

[60] Provisional application No. 60/008,117, Oct. 30, 1995.

[51] Int. Cl.$^6$ .................................................. G01N 33/06

[52] U.S. Cl. .................... 73/53.02; 73/864.81; 73/61.41; 73/61.71; 436/23; 422/74; 356/440; 356/435

[58] Field of Search ............................ 73/864.811, 53.02, 73/61.41, 61.44, 61.48, 61.59, 61.71; 436/22, 23; 422/74; 356/435, 436, 440; 99/452

[56] References Cited

U.S. PATENT DOCUMENTS

| | | | |
|---|---|---|---|
| 3,841,756 | 10/1974 | Grochowicz | 356/72 |
| 3,841,834 | 10/1974 | Gandhi et al. | 23/231 |
| 4,144,804 | 3/1979 | O'Keefe et al. | 422/74 |
| 4,497,898 | 2/1985 | Anderson et al. | 436/23 |

*Primary Examiner*—Hezron Williams
*Assistant Examiner*—Nashmiya Fayyaz
*Attorney, Agent, or Firm*—Morrison Law Firm

[57] ABSTRACT

The fat content and an undissolved solids content of a milk sample, taken from a milk processing flow, are separately determined. In addition, the total solids content of the milk flow is determined. Based on the fat, undissolved solids, and total solids content, the amount of protein and/or casein in the flow is determined. In a control portion of the invention, the fat and undissolved solids are controlled dynamically to standard values, whereby the characteristics of the milk flow are adjusted to standard values useable for whole milk, cheese-making and other uses.

8 Claims, 10 Drawing Sheets

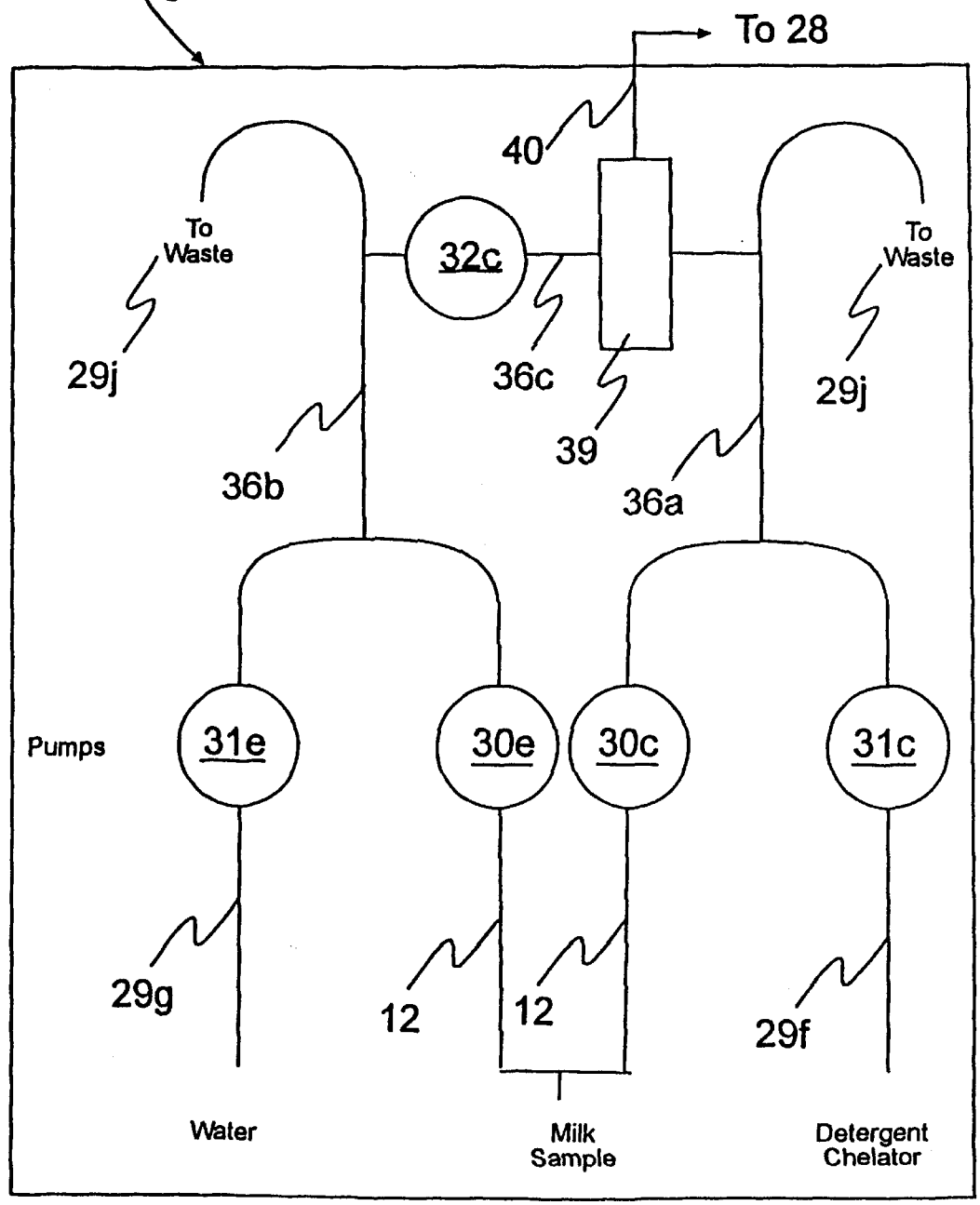

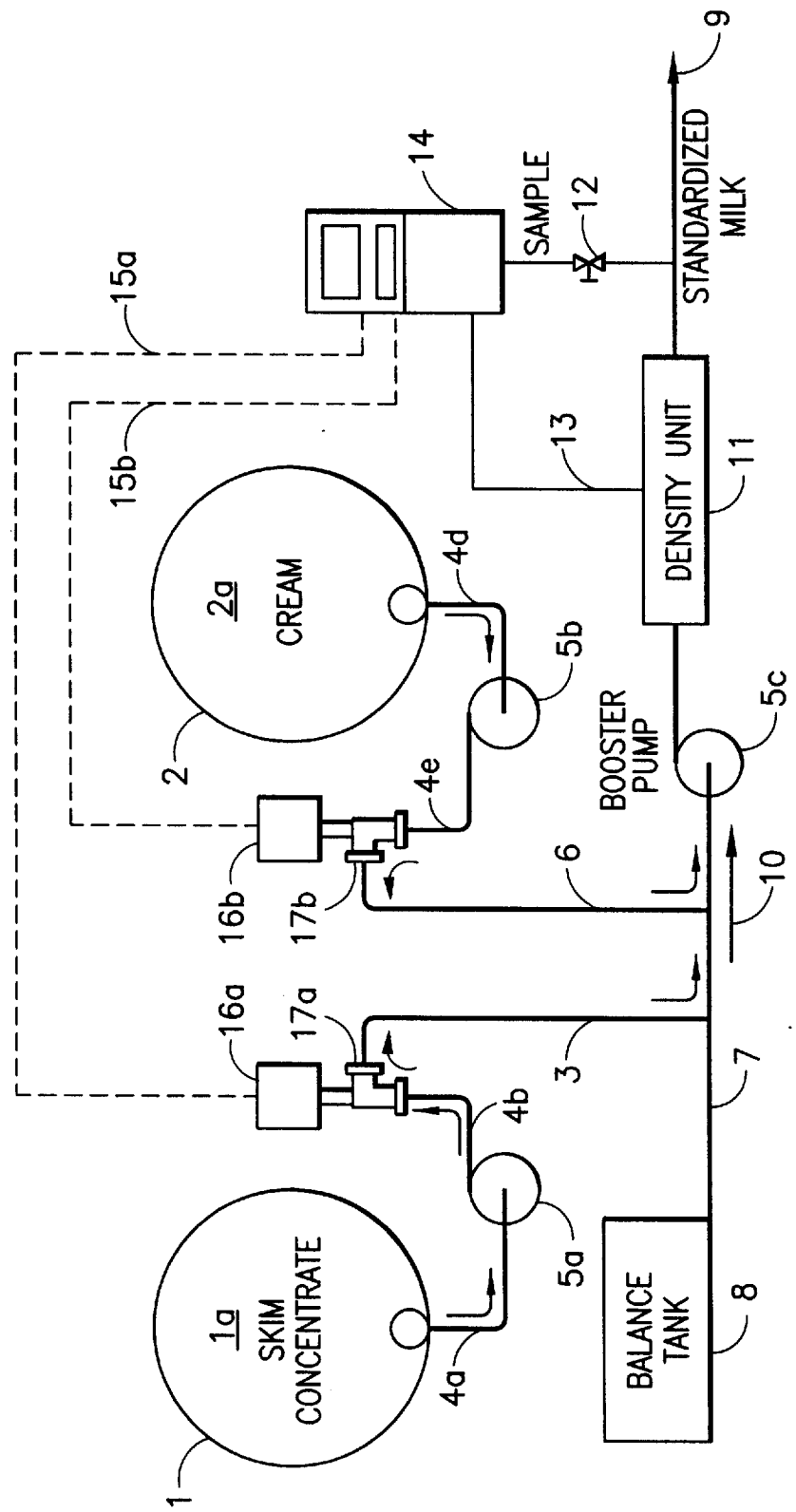

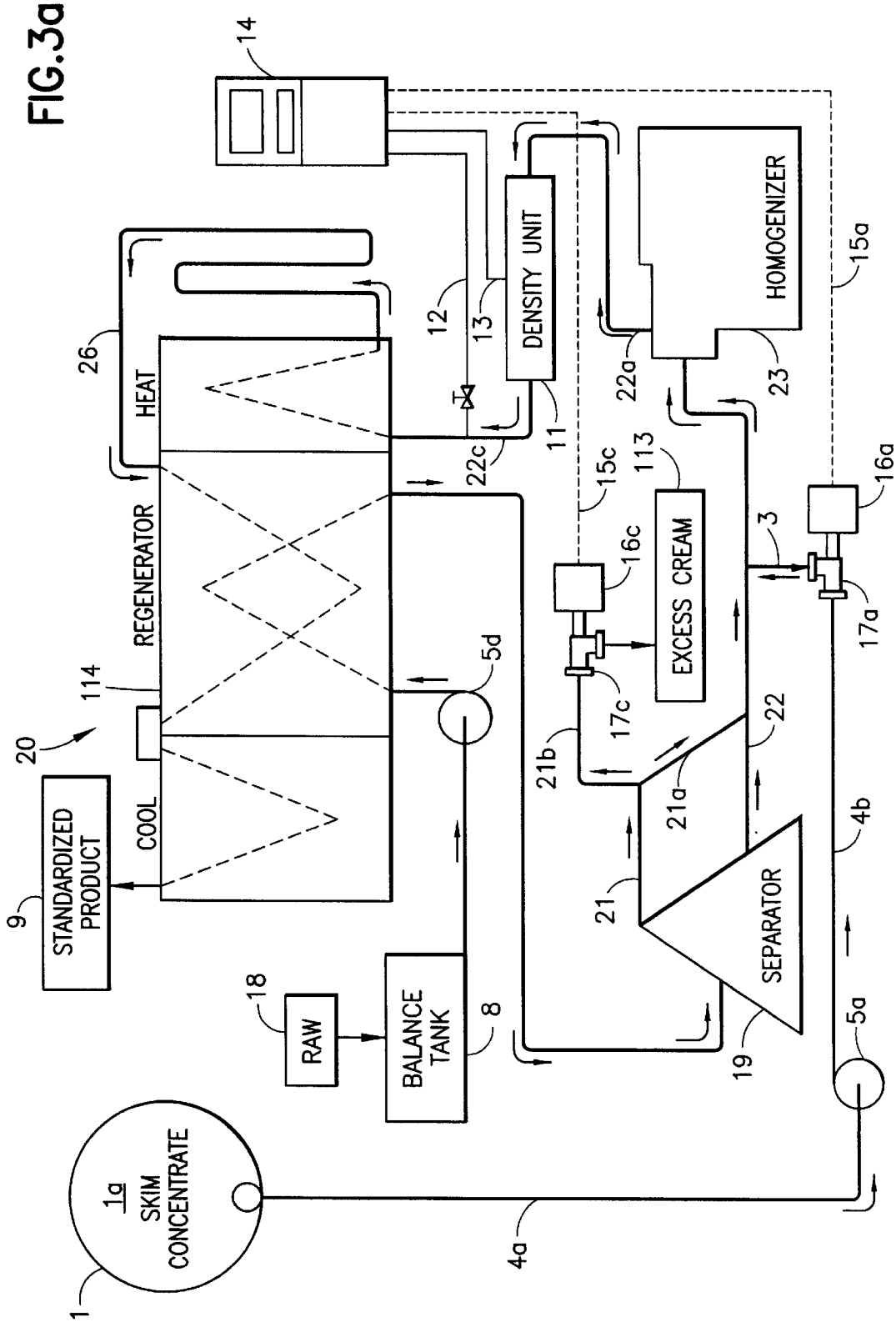

Protein = $(M_1)$(MAP)+$(M_2)$(Fat)+$(M_3)$(TS)+$(M_4)$(MAP)(Fat)+ $(M_5)$(MAP)(TS)+$(M_6)$(Fat)(TS)

Where:  M   =   coefficients
        MAP =   Micelle Associated Protein
        TS  =   Total Solids

2°

Protein = (Slope)(1° estimate) + bias

DEVICE AND METHOD FOR MEASURING, MONITORING, AND CONTROLLING FAT AND MICELL ASSOCIATED PROTEIN CONCENTRATION IN STANDARDIZED MILK

BACKGROUND OF THE INVENTION

This invention is related to the analysis of milk. Specifically, this invention is related to a device and method of determining the protein and fat content of milk for the purpose of producing milk with a predetermined ratio of protein and fat. More specifically, the present invention is related to a device and method for continuously monitoring the fat and micellar associated protein (MAP) content of milk, separated milk fractions, and reconstituted milk products in commercial type milk processing systems, and for controlling the ratio of fat to MAP in an output stream of these systems.

Milk consists primarily of water containing proteins, carbohydrates, electrolytes, lipids, and vitamins. The major proteins of milk are categorized as caseins, lactalbumins, and lactoglobulins, which include immunoglobulins. Milk lipids are mainly triacylglycerides containing the residues of various saturated and unsaturated, branched and straight chain fatty acids. In addition, some free fatty acids and phospholipids are also present.

In freshly secreted milk, lipids occur as butterfat globules. The fat globules, initially ranging in size from 1 to 15 um mean diameter, quickly begin to coalesce and separate under the force of gravity. Once the butterfat has separated out, the remaining fraction is skim milk.

Of the proteins, the lactalbumins and lactoglobulins (commonly known as whey proteins) are mostly soluble, while the caseins and a minor fraction of the other proteins take the form of complex micelles. Micelles and micelle-associated proteins (MAP) give skim milk its white appearance. The addition of detergent chelaters, such as ethylenediaminetetraacetic acid (EDTA), break down the micelles and render skim milk essentially clear.

The making of cheese is based on the coagulation of casein and the other MAPs from milk. The casein is precipitated from the whey by acidification, which can be accomplished by natural culturing, or the addition of rennet. The procedures for making cheese vary greatly resulting in numerous cheese products. The composition and handling of the original milk, bacterial flora, and starter culture provide the basic variables in cheese making. These basic variables, along with heat treatments, flavoring, salting, forming, and curing, determine the characteristics of the final product.

The type of cheese as well as the efficiency of production is critically influenced by the ratio of MAP to butterfat in the milk. Consequently, commercial dairy milk for successful cheese production must meet the specifications for fat-to-MAP ratio of the cheese manufacturer purchasing the milk. These specifications are often difficult to meet since each variety of cheese calls for a different fat-to-MAP ratio.

Numerous laboratory methods for determining fat and protein content in milk are known in the art. Fat concentration is routinely determined using the Babcock test or one of its modifications. Alternatively, other assay methods are employed, including the Mojonnier method, the Gerber test, and the TeSa test. In: "Laboratory Manual, Methods of Analysis of Milk and its Products", The Milk Industry Foundation, Washington D.C., 1959.

The protein content of milk and milk products can be determined by a variety of laboratory methods including gasometric assays, variations of the Kjedahl method, quantitative titration analysis, colorimetric assay, and dye binding and spectrophotometric optical analysis. However, these methods are too complex for routine use in a dairy plant. Consequently, measurement of milk protein content has seldom been used as a basis for commercialization in spite of the fact that cheese production is based on casein content.

Additionally, laboratory methods, adequate for commercial operations based on batch processing, are far too slow to be used with the current more commonly used continuous-flow systems. Continuous-flow equipment, which allows high product throughput, requires continuous rapid measurement of fat and protein content coupled with rapid feedback controls based on the monitored results. In these instances laboratory sampling is unreliable because the composition of the milk is constantly changing and the test sample becomes irrelevant by the time the laboratory results are complete.

A simple monitoring/control device responsive to fat content in continuous flow systems is known in the art. U.S. Pat. No. 4,144,804 describes an "Apparatus for Continuously Controlling Butterfat Content of Reconstituted Milk". U.S. Pat. No. 4,144,804 specifies an apparatus wherein milk is continuously sampled and diluted with a detergent chelator. The detergent chelator renders all components of the diluted milk transparent, except for the fat. The fat content is analyzed by absorbance of visible light in a spectrophotometric flow cell. In this system the butterfat content assay results are immediately available electronically and used as feedback for regulating valves that control the rate of butterfat reconstitution.

However, a simple system that is adaptable for monitoring and controlling protein content, or more specifically casein or MAP content, or casein or MAP to fat ratio, in continuous flow milk processing plants remains unknown in the art.

OBJECTS AND SUMMARY OF THE INVENTION

It is an object of the present invention to provide a simple method for determining micelle associated protein (MAP) content in milk.

It is a further object of the present invention to provide a device for continuously monitoring MAP content in milk processing.

It is yet a further object of the present invention to provide a method for monitoring and controlling MAP content as a function of fat content in milk at processing plants utilizing continuous flow equipment.

In the prior art, the fat content of milk is determined by making all components of the milk, except the fat, transparent, and then measuring the light transmittance of the remaining milk, thereby obtaining a measurement of the fat. In cheese-making, besides knowing the fat content, knowledge of the MAP content, and the ratio of fat to MAP is critical. In the present invention, the fat measurement is carried out as before. In addition, a measurement of total non-dissolved solids content, including both fat and MAP, is performed. Then, the fat content is subtracted from the total non-dissolved solids to determine the MAP content. A densitometer measurement gives the total solids in the milk (fat+undissolved solids+dissolved solids). As a result of these known values, all required characteristics of the milk are known with sufficient precision to permit dynamic control in a flow system.

According to an embodiment of the present invention there is provided a device for monitoring fat and protein content of standardized milk, comprising; a milk sample inlet, a first diluent reservoir, a second diluent reservoir, a diluent reservoir selector, the diluent reservoir selector connected to the first and second diluent reservoirs whereby a liquid contents of the first and second diluent reservoirs is able to flow into the diluent reservoir selector, at least one diluter having first and second diluter inlets and a diluter outlet, the first diluter inlet connected to the diluent reservoir selector whereby a diluent is able to flow into the first diluter inlet, the second diluter inlet connected to the milk sample inlet whereby milk sample is able to flow into the second diluter inlet, a spectrophotometer having at least one flow cell cuvette; and the diluter outlet being connected to the at least one flow cell cuvette whereby a diluted milk sample is able to flow into the at least one flow cell cuvette.

According to another embodiment of the present invention there is provided a device for monitoring and controlling fat and protein content of milk in a milk production system, comprising; a milk sample inlet, a first diluent reservoir, a second diluent reservoir, a diluent reservoir selector, the diluent reservoir selector connected to the first and second diluent reservoirs whereby a liquid contents of the first and second diluent reservoirs is able to flow into the diluent reservoir selector, at least one diluter having first and second diluter inlets and a diluter outlet, the first diluter inlet connected to the diluent reservoir selector whereby a diluent is able to flow into the first diluter inlet, the second diluter inlet connected to the milk sample inlet whereby milk sample is able to flow into the second diluter inlet, a spectrophotometer having at least one flow cell cuvette, the diluter outlet being connected to the at least one flow cell cuvette whereby a diluted milk sample is able to flow into the at least one flow cell cuvette, the spectrophotometer having means for outputting a signal responsively to a composition of a diluted milk sample contained in the at least one flow cell cuvette, a controller having means for receiving the signal from the spectrophotometer, and the controller having means for adjusting fat and protein composition of milk in the milk production system responsively to the signal.

According to another embodiment of the present invention there is provided a method for monitoring and controlling fat and protein content of milk in a milk production system, comprising the steps of;

executing a fat control sequence, including the steps of; obtaining a milk sample, measuring a fat concentration of the milk sample, comparing the fat concentration with a fat standard, generating a fat adjust signal responsively to a result of the comparing the fat concentration with the fat standard, sending the fat adjust signal to a fat adjusting means in the milk production system, operating the fat adjusting means responsively to the fat adjust signal, and pausing for a system equilibration, and executing a protein control sequence, including the steps of; obtaining a second milk sample, measuring a fat plus protein concentration of the second milk sample, subtracting the fat concentration from the fat plus protein concentration resulting in a protein concentration of the second milk sample, comparing the protein concentration with a protein standard, generating a protein adjust signal responsively to a result of the comparing the protein concentration with the protein standard, sending the protein adjust signal to a protein adjusting means in the milk production system, operating the protein adjusting means responsively to the protein adjust signal, and pausing for a system equilibration.

According to another embodiment of the present invention there is provided a method for measuring fat and protein content in milk comprising the steps of; splitting a sample of milk into first and second parts, diluting the first part with a detergent chelator, measuring a fat based light absorbance of the first part, comparing the fat based light absorbance with a fat standard light absorbance, calculating a fat concentration of the sample, diluting the second part with water, measuring a light absorbance of the second part, comparing the light absorbance with a fat-plus-protein standard light absorbance, calculating a fat-plus-protein concentration of the sample, and subtracting the fat concentration of the sample from the fat-plus-protein concentration of the sample.

According to another embodiment of the present invention there is provided a device for measuring fat and protein content in milk, comprising; a milk sampler, a diluter flowably connected to the milk sampler, and an analyzer flowably connected to the diluter.

According to another embodiment of the present invention there is provided a device for monitoring and controlling fat and protein content in standardized milk processing systems, comprising; a milk sampler flowably connected to a milk processing system, a diluter flowably connected to the milk sampler, an analyzer flowably connected to the diluter, the analyzer having an output, a controller connected to the milk processing system, the controller connected to the output, the controller having means for controlling fat and protein content in milk being processed by the milk processing system, and the means for controlling, controlling responsively to the output.

According to another embodiment of the present invention there is provided a milk measurement apparatus comprising; means for measuring a fat content of the milk, means for measuring an undissolved solids content of the milk, means for measuring a total solids of the milk, and means for determining, based on the fat content, the undissolved solids content and the solids content, at least a protein content of the milk.

According to another embodiment of the present invention there is provided a method for measuring characteristics of milk comprising; measuring a fat content of the milk, measuring an undissolved solids content of the milk, measuring a total solids of the milk, and determining, based on the fat content, the undissolved solids content and the solids content, at least a protein content of the milk.

The present invention is a device and method adapted for monitoring and/or controlling the butterfat and protein content in standardized milk. The invention is especially adaptable for standardization of milk for cheese production. The device consists of a sampling inlet feeding a milk sample into a diluter. The diluter has the ability to select an appropriate diluent for dilution that renders the milk sample analyzable by a spectrophotometer. For fat determination, the milk sample is diluted with a detergent chelating agent which breaks up micellar protein. Absorbance readings on the spectrophotometer of chelator-detergent diluted milk samples are concentration dependant on only the fat content. Dilution of the milk sample with water gives absorbance readings that are dependant on the concentration of fat plus micelle-associated proteins. The micelle associated protein concentration can then be obtained by subtracting the fat concentration from the total. The electronic output of the spectrophotometer is linked to a controller that controls the protein and fat content of the milk in the processing system responsively to the signal and in coordination with the fat and/or fat plus protein analysis.

Briefly stated, the fat content and an undissolved solids content of a milk sample, taken from a milk processing flow, are separately determined. In addition, the total solids content of the milk flow is determined. Based on the fat, undissolved solids, and total solids content, the amount of protein and/or casein in the flow is determined. In a control portion of the invention, the fat and undissolved solids are controlled dynamically to standard values, whereby the characteristics of the milk flow are adjusted to standard values useable for whole milk, cheese-making and other uses.

The above, and other objects, features and advantages of the present invention will become apparent from the following description read in conjunction with the accompanying drawings, in which like reference numerals designate the same elements.

BRIEF DESCRIPTION OF THE DRAWINGS

FIG. 1b is a schematic diagram to illustrate the operating principle for determining fat and MAP in the wet analysis testing section of the present invention.

FIG. 2 is a schematic diagram of a first system for producing standardized milk according to an embodiment of the invention.

FIG. 3a is a schematic diagram of a second system for producing standardized milk according to another embodiment of the invention.

FIG. 6b is an example of an algorithm, based on MAP, fat, and total solids, useful for calibrating the control component of the present invention.

DETAILED DESCRIPTION OF THE PREFERRED EMBODIMENTS

Figure 1A:
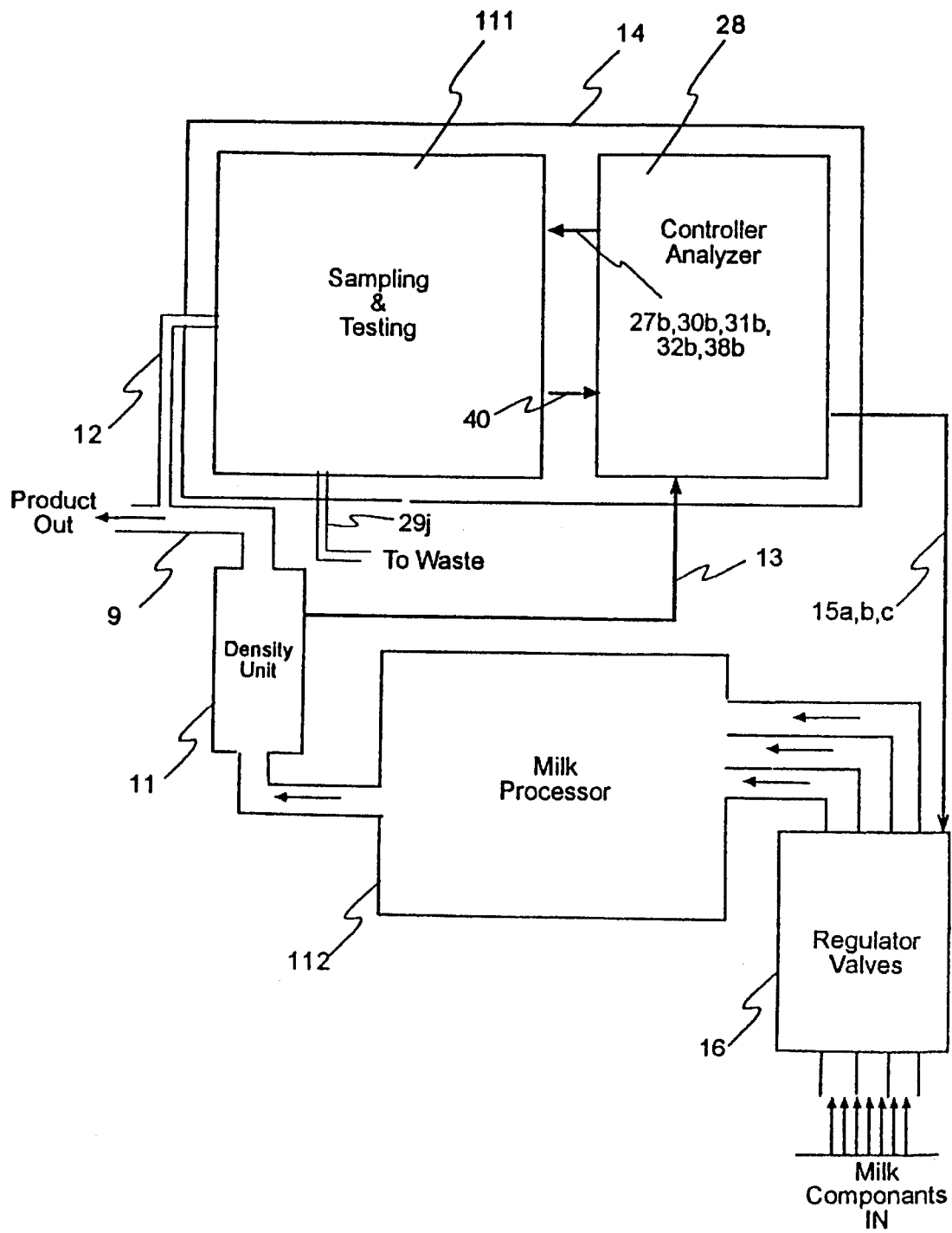
FIG. 1a is a functional block diagram to exemplify the general relationship of major components of the present invention.

Referring to FIG. 1a, a milk processing plant has an input point through which milk components enters the system regulated by regulator valves 16. The milk components then flow into a milk processor 112 where they combine and are processed into standardized milk. The standardized milk flows through a density unit 11 where specific gravity is measured. A sample of the standardized milk is then sampled and tested for MAP and fat by a sampling and testing component 111 of a controller testing device 14. Finally, the milk exits as finished product on an outflow line 9 ready for any post-processing procedures.

A digital controller analyzer 28 of controller testing device 14 receives a signal from density unit 11, representing the density of the outflowing milk, and a signal from sampling and testing component 111, representing the MAP and fat in the milk flow. Digital controller analyzer 28 responds to its input signals by producing output signals for controlling the flows of milk components admitted to the system by regulator valves 16.

Digital controller analyzer 28 also produces signals applied to sampling and testing component 111 for controlling valves and pumps therein, as will be explained.

Referring to FIG. 1b, sampling and testing component 111 receives a milk sample through a sample tube 12 and separately combines the milk sample, at an empirically determined dilution, with diluents. The diluents are water through a tubing 29g and detergent chelator solution through a tubing 29f. The ratios of milk to water and milk to detergent chelator solution is controlled by positive metering pumps, pumps 30e and 31e for milk to water mixture and 30c and 31c for milk to detergent chelator mixture. Milk and water, mixed in a mixing tube 36b, flow past one end of spectrophotometer tubing 36c to a waste tubing 29j. Likewise milk and detergent chelator, mixed in a mixing tube 36a, flow past the other end of spectrophotometer tubing 36c to waste tubing 29j. Spectrophotometer tubing 36c connects mixing tube 36a to mixing tube 36b through a reversible pump 32c and a flow cell spectrophotometer 39. During operation, switching from measuring the absorbance or transmittance of the milk/water mixture to measuring the absorbance or transmittance of the milk/detergent chelator mixture is accomplished by reversing reversible pump 32c to draw first one, and then the other component to be measured into spectrophotometer 39.

It would be apparent to one skilled in the art, in the light of the present disclosure that, instead of using reversible pump 32c with a single spectrophotometer 39, may use separate spectrophotometers for continuous measurement of the parameters of interest of both mixtures.

Referring to FIG. 2, a balance tank 8 contains a liquid, either skim milk or water. A booster pump 5c draws a constant supply of the liquid from balance tank 8 on a milk pipe 7. As the liquid passes through milk pipe 7, metered amounts of skim concentrate and cream are added to produce standardized milk.

A storage tank 1 contains a previously processed skim milk concentrate 1a. Skim milk concentrate 1a is normal skim milk from which a substantial proportion of water has been removed. A skim pump 5a draws skim milk concentrate from storage tank 1, through a pipe 4a. The skim milk concentrate under pressure from skim pump 5a passes through a pipe 4b to a skim screw 17a. A pipe 3 connects a metered amount of skim concentrate from skim screw 17a to milk pipe 7. Skim screw 17a is a metering valve that meters the rate that skim concentrate 1a flows through pipe 3 and is added to the liquid flowing in milk pipe 7.

Simultaneously, a previously processed supply of a cream 2a, in a storage tank 2, is drawn by a cream pump 5b through a pipe 4d. Cream under pressure from cream pump 5b passes through a pipe 4e to a cream screw 17b. A pipe 6 connects a metered amount of cream from cream screw 17b to milk pipe 7. Cream screw 17b is a metering valve that meters the rate that cream 2a flows through pipe 6 and is added to the liquid flowing in milk pipe 7.

The skim concentrate flowing from line 3 and cream flowing from line 6 mix with the liquid in line 7, the mixture of which forms the standardized milk. The standardized milk is pumped by booster pump 5c in the direction of an arrow 10 through a density measuring unit 11 to outflow line 9. An electronic output 13, representing the density of the standardized milk, is fed from density measuring unit 11 to a signal input of controller testing device 14. Additionally, a small sample of the standardized milk passing through outflow line 9 is fed through sample tube 12 to controller testing device 14. Controller testing device 14 determines the butterfat concentration and casein concentration of the sample of standardized milk from outflow line 9.

Measured butterfat and casein concentration along with measured density of standardized milk in outflow line 9 are compared with operator input standards to produce control signals that are applied on controller leads 15a and 15b to screw controllers 16a and 16b respectively. In response to the signal on skim controller lead 15a, skim screw controller 16a operates skim screw 17a to adjust the flow of skim milk concentrate from skim concentrate storage tank 1 through pipe 3 to mix with the other components in milk pipe 7. Likewise in response to the signal on cream controller lead 15b, cream screw controller 16b operates a cream screw 17b to adjust the flow of cream through pipe 6 to mix with other components in milk pipe 7. This measuring and adjusting process occurs dynamically to maintain the casein to butterfat ratio in the standardized milk in outflow line 9 in balance with the operator input standards.

Referring to FIG. 3a, a second embodiment of the present invention, instead of mixing a previously separated cream supply with skim milk, separates skim milk from cream, and then combines the separated skim milk with the cream in a desired concentration to produce the desired concentration. Provisions include the addition of skim concentrate and the diversion of excess cream from the process, so that the standardized milk issuing from the system has the desired relationships of MAP and butterfat. A final step in the process includes conventional pasteurization to produce a pasteurized standardized milk.

Raw milk 18, entering the system through balance tank 8, is pumped by pump 5d through a regenerator 114 of a pasteurizer 20 into a cream separator 19. Still under pressure of pump 5d, raw milk 18 is separated into cream and skim milk. Cream exits the top of separator 19 through a cream line 21, and skim milk exits the bottom of separator 19 directly into a mixing line 22. Cream line 21 forks into a cream line 21a and a cream bleed line 21b. Cream bleed line 21b diverts a metered portion of the cream to cream screw 17c, so that the amount of cream remaining in cream line 21a is the amount required to produce the desired product. The cream passing cream screw 17c flows out at a metered rate to an excess cream tank 113. Cream screw 17c differs from cream screw 17b of FIG. 2 in that cream screw 17b meters the amount of cream flowing into milk pipe 7 where cream screw 17c meters the amount of cream removed from cream line 21. The cream removed from cream line 21 represents the cream in excess of that needed to produce the standardized milk.

As in FIG. 2, the milk in mixing line 22 is also supplemented, through pipe 3, with skim milk concentrate 1a under pressure of pump 5a at a rate determined by skim screw 17a. These additive steps, of controlling the amount of cream added from cream line 21a and skim milk concentrate added from pipe 3 in mixing line 22, adjust the cream and MAP concentrations in the standardized milk to the level desired in the final product.

The standardized milk flowing from mixing line 22 is homogenized in a warm milk homogenizer 23 and fed to density unit 11 through a line 22a. The density of the milk in density unit 11 is determined and a signal sent through electronic output lead 13 to controller testing device 14.

Milk flowing out of density unit 11, on a line 22c, is sampled through sample tube 12 for colorimetric determination of fat and micellar associated protein (MAP) concentrations by controller testing device 14. The determined concentrations of cream and MAP are compared with standards. If the concentration of either varies from the standard a quantitative signal is generated to adjust valves 17a and 17c as appropriate. For example, if the cream concentration is higher than that of the standard, a quantitative signal is sent on line 15c to cream screw controller 16c which responds by adjusting cream screw 17c to allow more cream to be diverted to excess cream tank 113. Conversely, if the cream concentration is lower than that of the standard, a quantitative signal is sent on line 15c to cream screw controller 16c which responds by adjusting cream screw 17c to allow less cream to be removed to excess cream tank 113. Similarly, if the concentration of MAP differs from the standard, a quantitative signal is sent on line 15a to skim screw controller 16a which responds by adjusting skim screw 17a to thereby adjust the amount of skim concentrate added.

After sampling, the milk is pasteurized by pasteurizer 20 and flows out as the finished product, standardized milk, through outflow line 9.

Figure 3B:
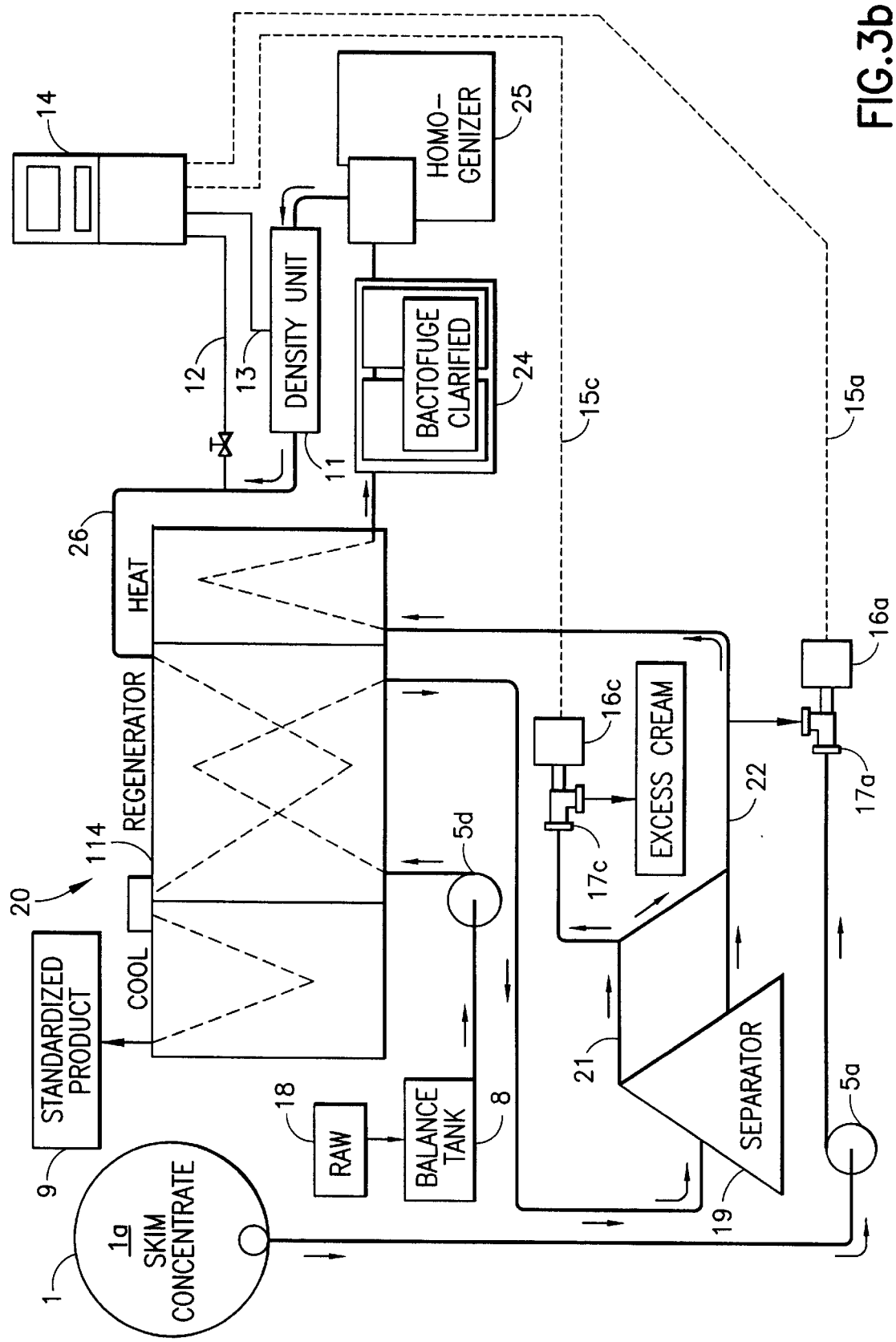
FIG. 3b is a schematic diagram of a third system for producing standardized milk according to yet another embodiment of the invention.

Referring to FIG. 3b, a third embodiment of the present invention producing standardized milk for cheese manufacture differs from the second embodiment in that a bactofuge clarifier 24 and a hot milk homogenizer 25 are utilized on a hot loop 26 of pasteurizer 20. Warm milk homogenizer 23 is omitted in this system. Sampling occurs through sample tube 12 taken from hot loop 26 after the milk has passed bactofuge clarifier 24, homogenizer 25, and density measuring unit 11. The sampling point is located after the homogenizer on hot loop 26 because a small amount of skim milk is lost during bacteria removal by bactofuge clarifier 24. In contrast, in the embodiment of FIG. 3a, homogenizer 23, and density measuring unit 11 and sample tube 12 are all located upstream of pasteurizer 20, and thereby operate on cooler milk.

Figure 4:
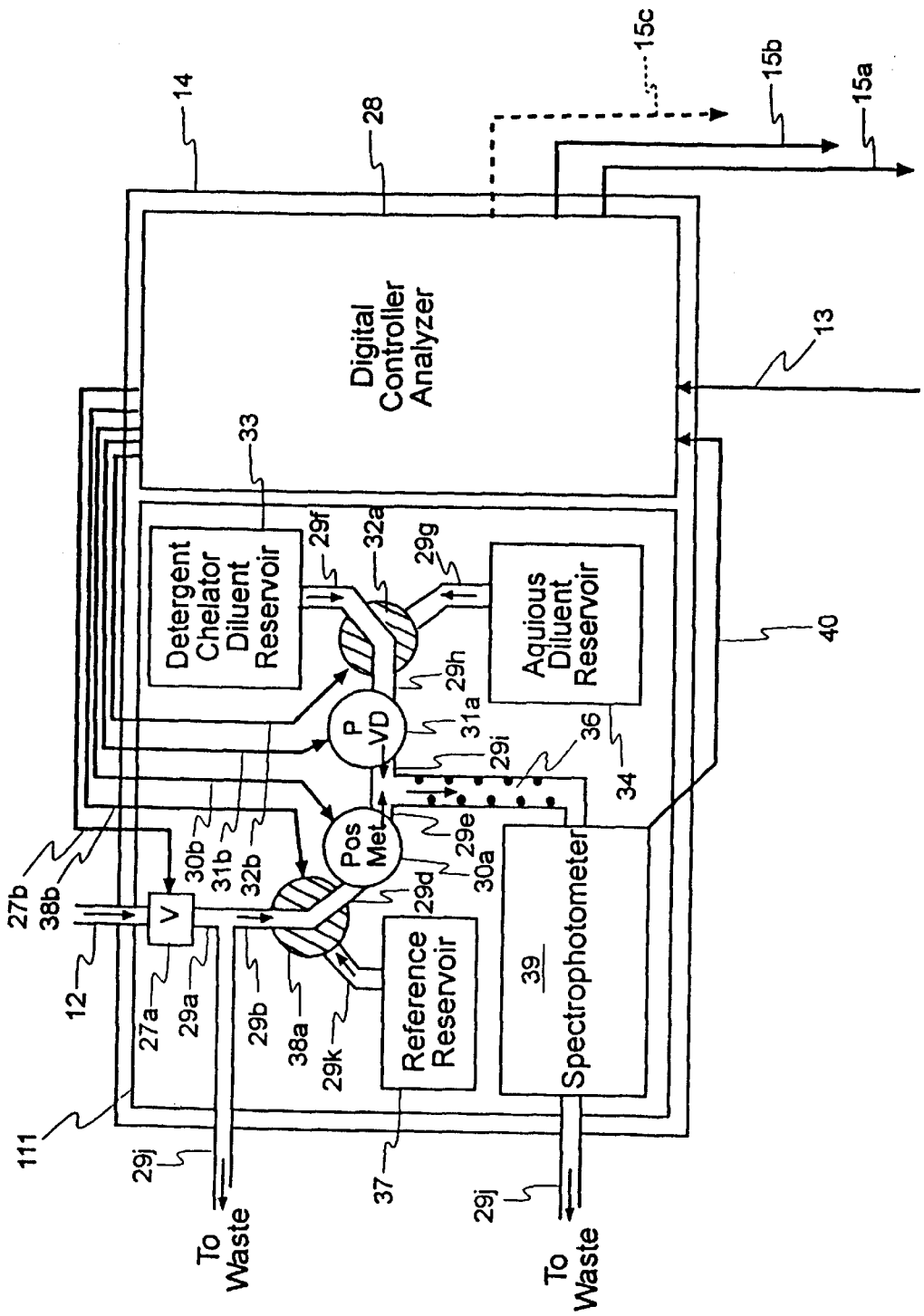
FIG. 4 is a schematic diagram illustrating an example of a controller testing device portion utilized in the present invention.

Referring to FIG. 4, sampling and testing component 111 receives milk form sampling tube 12 controlled by a valve 27. At a predetermined time, when a sample is to be tested, digital controller analyzer 28 sends a signal on a lead 29 causing valve 27 to open. Sample milk flows into a tubing 29a under pressure of the production system. The portion of the sample to be ultimately tested flows into a tube 29b, while excess sample flows to waste through a tube 29j. The milk sample flows through a sample selection valve 38a operated by digital controller analyzer 28 through a selection valve control lead 38b. From sample selection valve 38a the production sample flows through a tubing 29d to a positive metering sample pump 30a. Sample pump 30a is controlled by digital controller analyzer 28 over a sample pump control lead 30b.

Simultaneously with the activation of sample pump 30a, a diluent pump 31a is activated. Diluent pump 31a is under the control of digital controller analyzer 28. The diluent to be used is selected by a diluent selection valve 32a from either a first diluent reservoir 33 and a second diluent reservoir 34. Diluent selection valve 32a is under the control of digital controller analyzer 28 through a diluent selection valve control lead 32b. First diluent reservoir 33 is connected to diluent selection valve 32a by tubing 29f. Second diluent reservoir 34 is connected to diluent selection valve 32a by tubing 29g. Diluent selection valve 32a is connected to positive metering diluent pump 31a by a tubing 29h.

A specified flow of sample is pumped by sample pump 30a through a tube 29e to mixing a junction 35.

Simultaneously, a specified flow of diluent is pumped by diluent pump 31a through a tube 29i to mixing junction 35. The sample and diluent continue to mix in a mixing tube 36 to produce an optically homogeneous mixture.

The diluted sample flows from mixing tube 36 into spectrophotometer 39. Spectrophotometer 39 produces a quantitative absorbance signal responsively to the optical density of the diluted sample. The absorbance signal from spectrophotometer 39 is communicated over absorbance output lead 40 to digital controller analyzer 28. After passing through spectrophotometer 39 the diluted sample flows to waste through tubing 29j.

The absorbance signal received from spectrophotometer 39 is analyzed and compared with a stored standard signal by digital controller analyzer 28. If the sample signal and the stored standard signal are not equal then digital controller analyzer 28 causes an appropriate adjustment in cream or skim screw controllers 16a, 16b, or 16c.

For calibration, the process described above may be performed on a reference sample stored in a reference reservoir 37. That is, selector valve 38a may be actuated to substitute the reference sample for the sample. By comparing the output produced by the reference sample with the normal sample, the apparatus may be calibrated accurately.

Skim screw 17a and cream screws 17b, 17c are, for example, 3000 position valves operated by stepper motors. A signal coming from digital controller analyzer 28 contains a directional component and a number representing a quantity of steps to be executed by each stepper motor. If for example skim screw 17a is adjusted, the directional component instructs skim screw controller 16a to either open or close the valve and the quantity of pulses would determine the number of steps the valve is to be moved. Skim screw controller 16a then operates the stepper motor of skim screw 17a accordingly.

Figure 5:
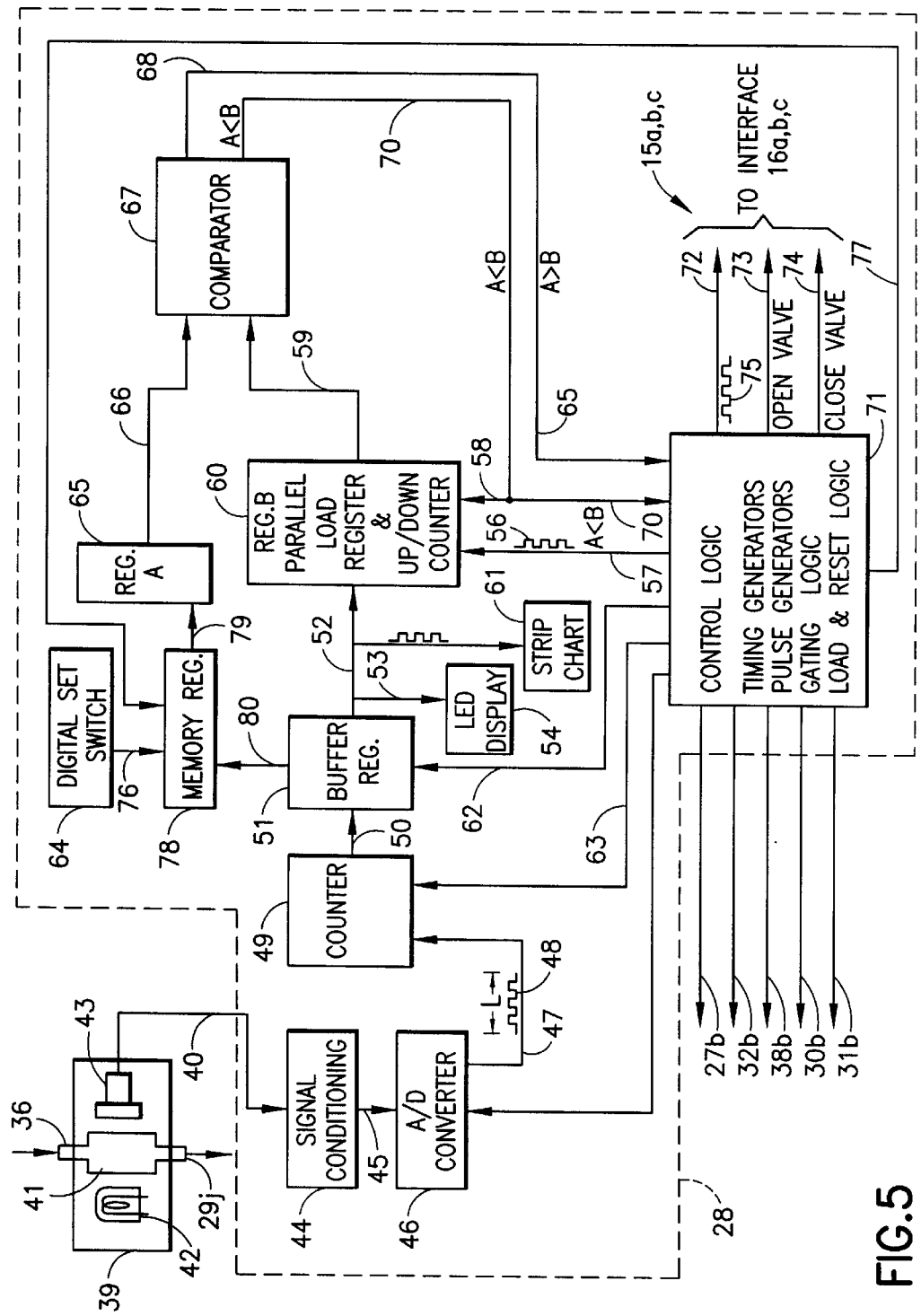
FIG. 5 is functional block diagram of the digital controller analyzer interaction with the wet analysis testing portion of the present invention a feed back control system.

Referring to FIG. 5, a block diagram illustrates the functional connections of digital controller analyzer 28 with spectrophotometer 39 and the various valves and pumps that fall under the control of digital controller analyzer 28. Digital controller analyzer 28 controls the selector valves and positive metering pumps that operate the sampling and analysis function of controller testing device 14. Responsively to the constantly updated results from the analysis function, digital controller analyzer 28 also adjusts cream and skim screws 17a, 17b, and 17c.

Spectrophotometer 39 includes a light source 42. Light emitted from light source 42 is focused to pass through a flow cell cuvette 41 to strike a photodetector 43. The light absorbed as it passes through flow cell cuvette 41 is proportional to the concentration of the opaque particles in the sample. Photodetector 43 generates an analog signal responsively to the intensity of light striking it. When diluent alone flows through flow cell cuvette 41, very little light is absorbed and a large analog signal is generated by photodetector 43. When a diluted milk sample flows through flow cell cuvette 41, more light is absorbed and a smaller analog signal is generated by photodetector 43. The amount of light absorbed and consequently the size of the signal generated depends on the concentration of absorbing substances flowing through cuvette 41. In milk, both fat globules and micellar associated proteins (MAP) are able to absorb light.

The analog signal generated by spectrophotometer 39 enters digital controller analyzer 28 over absorbance output lead 40. The measured analog signal is applied to a signal conditioning circuit 44 where the analog signal is continuously amplified and linearized. Signal conditioning circuit 44 may include integrated circuit operational amplifiers (IC Op Amps) and integrated circuit linearization modules to produce a 0–5 VDC signal. The 0–5 VDC is applied over a line 45 to an A/D converter 46. A/D converter 46 is operative to convert the continuous analog input to a TTL compatible digital pulse train 48 at its output line 47. Digital pulse train 48 has a number of pulses L related to the measured absorbance in the linear range of spectrophotometer 39. For example, each pulse in the pulse train may correspond to 0.03% absorbance. The gateing signal, i.e. the start and stop signals for generation of pulse train 48 is provided by a control logic circuit 71. The start signals may be given typically at 30, 60, 90, or 120 second intervals.

Pulse train 48 is sent over line 47 to a counter 49. Counter 49 is a low stage decimal counter that produces a four digit BCD code at its output line 40. Counter 49 may typically include a TTL 7490 circuit. Counter 49 counts the number of pulses L in pulse train 48, converts the result to BCD format in four significant figures, and produces a parallel output to a line 50. This output amounts to 16 bits of digital information. Control logic circuit 71 applies a reset signal for resetting counter 49 on a line 63.

The 16 bit output of counter 49 is fed over line 50 to a buffer register 51 which stores the sixteen bit information until a subsequent 16 bit output from counter 49 overwrites it. Four stage buffer register 51 produces four digit output in BCD code to a line 52 and may include a TTL 74175 circuit. Buffer register 51 is loaded following a command signal provided over a line 62 by control logic circuit 71. The command signal is generated following completion of each new analog to digital conversion by A/D converter 46. The output of buffer register 51 on line 52 is applied to an LED display via a line 53 and a strip chart recorder 61 via a line 55.

The output of buffer register 51 on line 52 is applied to a Reg. B 60. Reg. B 60 includes a parallel load register, an up/down counter, and may typically have a TTL 74190 circuit. On command, in the form of a pulse train signal 56 on a lead 57 from control logic circuit 71, the four digit information output from buffer register 51 is loaded into Reg. B 60. The loaded information may be counted up or down depending on the count direction control signal applied to Reg. B 60 via line 70. The output of Reg. B 60 is applied through a line 59 to a comparator 67. Comparator 67 may typically include a TTL 7485 circuit.

The desired concentrations of MAP and fat are entered, either manually or automatically, by actuation of a digital set switch 64. Values entered into digital set switch 64 are transferred in three digit parallel BCD form over a line 76 to memory locations in a memory register 78. Memory register 78 includes at least two memory locations and a summing circuit. Control logic circuit 71 selects a memory register and causes a value to be loaded into that selected memory location by sending appropriate signals down a line 77. For example, if desired fat concentration is being entered, control logic circuit 71 causes the output of digital set switch 64 to be stored in a first memory location. If desired MAP concentration is being entered, control logic circuit causes the summing circuit of memory register 78 to add the value at first memory location with the output of digital set switch 64 and store the result in a second memory location.

Alternatively, the values at first and second memory location may be obtained during calibration from buffer register 51. In this case the value in buffer register 51 may be loaded over a lead 80 to an appropriate location of memory register 78 according to a command signal from control logic circuit 71 on line 77. If the known concentration of fat is the standard measured at spectrophotometer 39 then control logic circuit 71 over line 77 causes the value in buffer register 51 to be loaded into the first memory location of memory register 78. Likewise, if the standard measured at spectrophotometer 39 is concentration of fat plus MAP, the value in buffer register 51 is loaded into the second memory location of memory register 78.

The value in memory register 78, appropriate for the measurement being taken at spectrophotometer 39, is directed by a command signal over line 77 from control logic circuit 71 to be applied over a line 79 to a Reg. A 65. Reg. A 65, which may typically include a TTL 74L98 circuit, produces a four digit output signal corresponding to the value loaded from memory register 78. This four digit signal, a sixteen-bit information output, is applied over a line 66 to comparator 67.

Comparator 67 continuously compares, at appropriate intervals (for example 30, 60, 90, or 120 sec.), the sixteen bit information input from Reg. A 65 with the sixteen bit information input from Reg. B 60. Comparator 67 subsequently outputs the result of the comparison to control logic circuit 71 over output lines 68 or 70. If the value in Reg. A 65 is greater or less than the value in Reg. B 60 then comparator 67 sends a signal down output lead 68 or 70 respectively. If the values in Reg. A 65 and Reg. B 60 are the same, there will be no output signal on either of output lines 68 or 70.

Referring again to FIG. 4 in the context of FIG. 5, control logic circuit 71, of digital controller analyzer 28, includes timing generators, pulse generators, gateing logic, load and reset logic circuits, and sample testing sequence logic. Control logic circuit 71 operates;

to send signals over lead 27b to open and close a sampling valve 27a, to send signals over lead 38b to operate selector valve 38a, to coordinate the operation of selector valve 38a with calibration and memory storage functions, to send signals over lead 32b to operate diluent selection valve 32a, to coordinate the operation of diluent selection valve 32a with the transfer of appropriate values (either butterfat measurement or MAP measurement) from memory register 78 to Reg. A 65 which results in the adjustment of the appropriate digital valve 17 (screw 17a, 17b, or 17c), to control the pulse rate of the signals sent to positive metering pumps 30a and 31a so that the correct dilution of sample milk results, and to feed signals down the appropriate line 15 (15a, 15b, or 15c) responsively to signals received from comparator 67, including a pulse train 75 on a line 72, open valve direction signal on an open valve lead 73, and close valve direction signal on a close valve lead 74, and to gate pulse train 56, which is applied to Reg. B 60, and pulse train 75, which is applied to valves 16a, 16b and 16c.

Figure 6A:
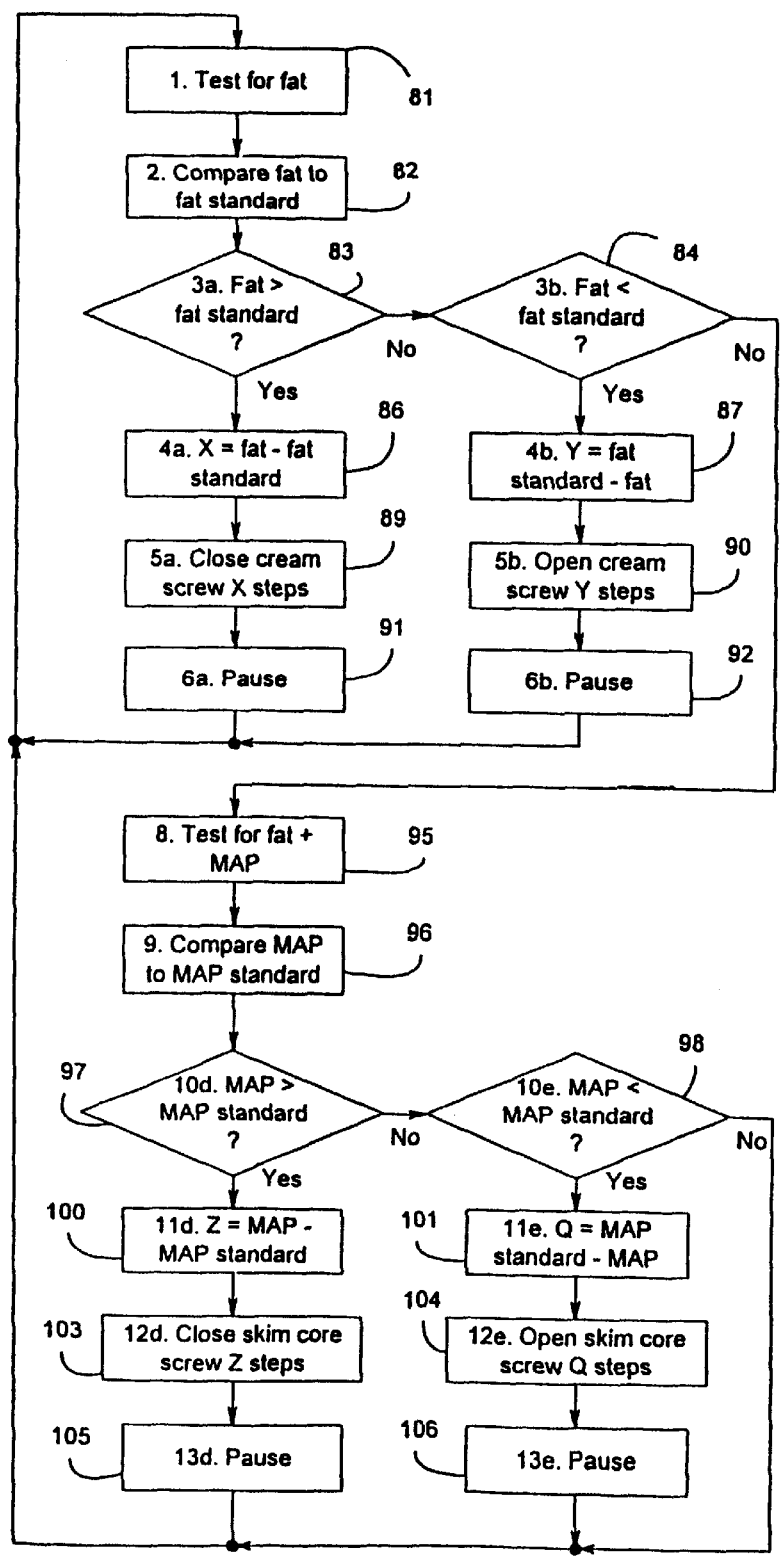
FIG. 6a is a flow chart of the step-wise process for testing and controlling the content of fat and micelle associated protein in processed milk.

Referring to FIG. 6a in the context of FIGS. 3–5, a decision tree flow chart is presented for the step-wise process whereby digital controller testing device 14 monitors and regulates the processing of standardized milk for cheese production.

In a running production system the milk is monitored for fat concentration and micelle associated protein (MAP) concentration. If either fat or MAP concentration falls outside the desired range, the system's regulator valves 16 (screws 17a, 17b, and 17c) is adjusted to correct the deficiency or remove the excess. During active production a small amount of the product at an appropriate stage is continuously bled off through sample tube 12 and arbitrarily enters the cyclical monitoring feedback process at a stage, step one 81, when digital controller testing device 14 is set to test for fat concentration. At this stage diluent selector valve 32a is set to utilize a detergent chelator diluent such as EDTA in the analysis. Detergent chelators break up micelles, thereby eliminating the influence of MAP on the absorbance reading. Since the sample is taken after the milk has been homogenized the fat particles are homogeneously sized and distributed uniformly throughout the sample. The uniform size and uniform distribution of the fat particles permits measurement of fat by the simple process of measuring light transmittance through a cuvette of a spectrophotometer. Positive metering pumps 30a and 31a dilute the sample to produce an absorbance value within the linear response range of spectrophotometer 39 (such as a 1:10 dilution).

Once the value for fat concentration is determined by the absorbance at spectrophotometer 39 the value is compared, at step two 82, with a standard value. The standard value can be a value obtained from the direct reading of milk known to contain the desired amount of fat. Alternatively, the standard value can be an electronic stored value based on previous production experience. The comparison is made by comparator 67 and the result obtained is fed to control logic circuit 71.

Three outcomes are possible. The fat concentration of the sample can be greater than that of the standard resulting in following the sequence beginning with step 3a 83 (hereafter sequence A). The fat concentration of the sample can be less than that of the standard resulting in following the sequence beginning with step 3b 84 (hereafter sequence B). The fat concentration of the sample can be the same as that of the standard.

If sequence A is followed, the product being produced has more than the desired amount of fat. At step four 86 the standard value is subtracted from the test value by control logic circuit 71 resulting in value X, and a pulse train is generated. Since the value is standardized in units such that one unit value is equivalent to the change in product content affected by opening or closing a digital valve one step, the number of pulses generated becomes the number of steps the valve moves. Therefore the pulse train with X pulses is sent down lead 72 of line 15c to cream screw controller 16c. In sequence A, too much cream, cream screw 17c is opened to bleed off more cream. Therefore, the directional signal is sent down open valve lead 73 of line 15c. In step 5a 89, as a result of these signals on line 15c, cream screw controller 16c adjusts cream screw 17c X steps in the opening direction. After a pause, step six 91, to allow the system to stabilize at the new setting, digital controller testing device 14 resets to step one 81.

If sequence B is followed, the product being produced has less than the desired amount of fat. At step four 87 the test value is subtracted from the standard value by control logic circuit 71 resulting in value Y, and a pulse train is generated. The pulse train with Y pulses is sent down lead 72 of line 15c to cream screw controller 16c. In sequence B, not enough cream, cream screw 17c is adjusted Y steps in the closing direction to bleed off less cream. Therefore, the directional signal is sent down close valve lead 74 of line 15c. In step 5b 90, as a result of these signals on line 15c, cream screw controller 16c adjusts cream screw 17c Y steps in the closing direction. After a pause, step six 92, to allow the system to stabilize at the new setting, digital controller testing device 14 resets to step one 81.

In the case at step two 82, where the fat in the sample is the same as the fat standard, the amount of fat in the milk being produced is correct. Therefore, no adjustments are made and digital controller testing device 14 advances to step eight 95.

At step eight 95 the amount of micellar associated protein (MAP) is tested. This procedure assumes that the fat concentration is stabilized at the concentration of the standard. This is because the reading at spectrophotometer 39 is for the total of fat plus MAP requiring the subtraction of fat concentration in order to obtain MAP concentration. If the fat in the product is standardized, then it is convenient to use that standard value as a constant in the MAP determination.

Although it is convenient to first stabilize the fat content at a standard value before beginning control of MAP, this sequence is not required. Simultaneous control of fat and MAP may be performed without departing from the spirit and scope of the invention.

At this stage diluent selector valve 32a is set to utilize water in the analysis. Water does not effect micelles so both fat and MAP are included in the absorbance reading. Since the sample is taken after the milk has been homogenized the fat particles are homogeneously sized and distributed throughout the sample. Positive metering pumps 30a and 31a are set to result in a dilution of the sample that produce a measurement value within the linear response range of spectrophotometer 39 (such as a 1:10 dilution).

Once the value of MAP plus fat has been determined by the absorbance at spectrophotometer 39 the value is compared, at step nine 96, with the standard value for MAP plus the standard value for fat. The standard value can be a value obtained from the direct reading of milk known to contain the desired concentration of MAP plus the standard concentration of fat. Alternatively, the value can be a stored electronic value based on previous production experience. The comparison is made by comparator 67 and the result obtained is fed to control logic 71.

Three outcomes are possible. The MAP plus standard fat concentration of the sample can be greater than that of the standard resulting in following the sequence beginning with step 10d 97 (hereafter sequence D). The MAP plus standard fat concentration of the sample can be less than that of the standard resulting in following the sequence beginning with step 10e 98 (hereafter sequence E). Finally, The fat concentration of the sample can be the same as that of the standard.

If sequence D is followed, the product being produced has more than the desired amount of MAP. At step eleven 100 the standard value is subtracted from the test value by control logic circuit 71 resulting in value Z. A pulse train is generated responsive to Z. As in the fat determination, the value Z is standardized in units such that one unit value is equivalent to the change in product content affected by opening or closing the digital valve one step. The number of pulses generated is the number of steps the valve moves. Therefore a pulse train with Z pulses is sent down lead 72 of line 15a to skim screw controller 16a.

In sequence D, too much skim concentrate, skim screw 17a is closed. Therefore the directional signal is sent down close valve lead 74 of line 15a. In step 12d 103, as a result of these signals on line 15a, skim screw controller 16a adjusts skim screw 17a Z steps in the closing direction. After a pause, step 13d 105, to allow the system to stabilize at the new setting, digital controller testing device 14 resets to step one 81.

If sequence E is followed, the product being produced has less than the desired amount of MAP. At step lie 101 the test value is subtracted from the standard value by control logic circuit 71 resulting in value Q. A pulse train containing Q pulses is sent down lead 72 of line 15a to skim screw controller 16a. In sequence E, not enough skim concentrate, skim screw 17a is opened. Therefore the directional signal is sent down open valve lead 73 of line 15a. In step 12e 104, as a result of these signals on line 15a, skim screw controller 16a adjusts skim screw 17a Q steps in the opening direction. After a pause, step 13e 106, to allow the system to stabilize at the new setting, digital controller testing device 14 resets to step one 81.

In the case at step nine 96, where the MAP equals the standard, the amount of MAP in the milk is correct. Therefore, no adjustments are made and digital controller testing device 14 resets to step one 81.

Referring to FIG. 6b, an example is given of an algorithm for calculating protein (casein) concentration based on measured concentrations of butterfat (fat), micelle associated proteins (MAP), and total solids (TS). The algorithm accounts for the two-way interaction effects of fat with MAP, fat with TS, and MAP with TS. Although a small effect exists from a three-way interaction of fat, TS, and MAP, this interaction is found in practice to be sufficiently small to be ignored. In practice, the best possible estimates of the coefficients are determined using a large data set of samples representative of those to be tested. This model becomes the primary calibration equation (1°). A secondary equation 2°, used for routine calibration, is a simple regression analysis of estimates of a few reference protein values against estimates from primary equation 1°. Only the slope and bias of secondary equation 2° is changed as a result of routine calibration. Primary equation 1° remains fixed unless the characteristics of the milk changes significantly.

Since fat concentration is critical to the determination of MAP concentration, digital controller testing device 14, utilizing a single beam spectrophotometer shown in FIG. 4, is always reset in FIG. 6a to step one 81 to retest for fat after each MAP test sequence. However, if a duel beam spectrophotometer is utilized in digital controller testing device 14 then fat and MAP plus fat can be monitored simultaneously.

Figure 7:
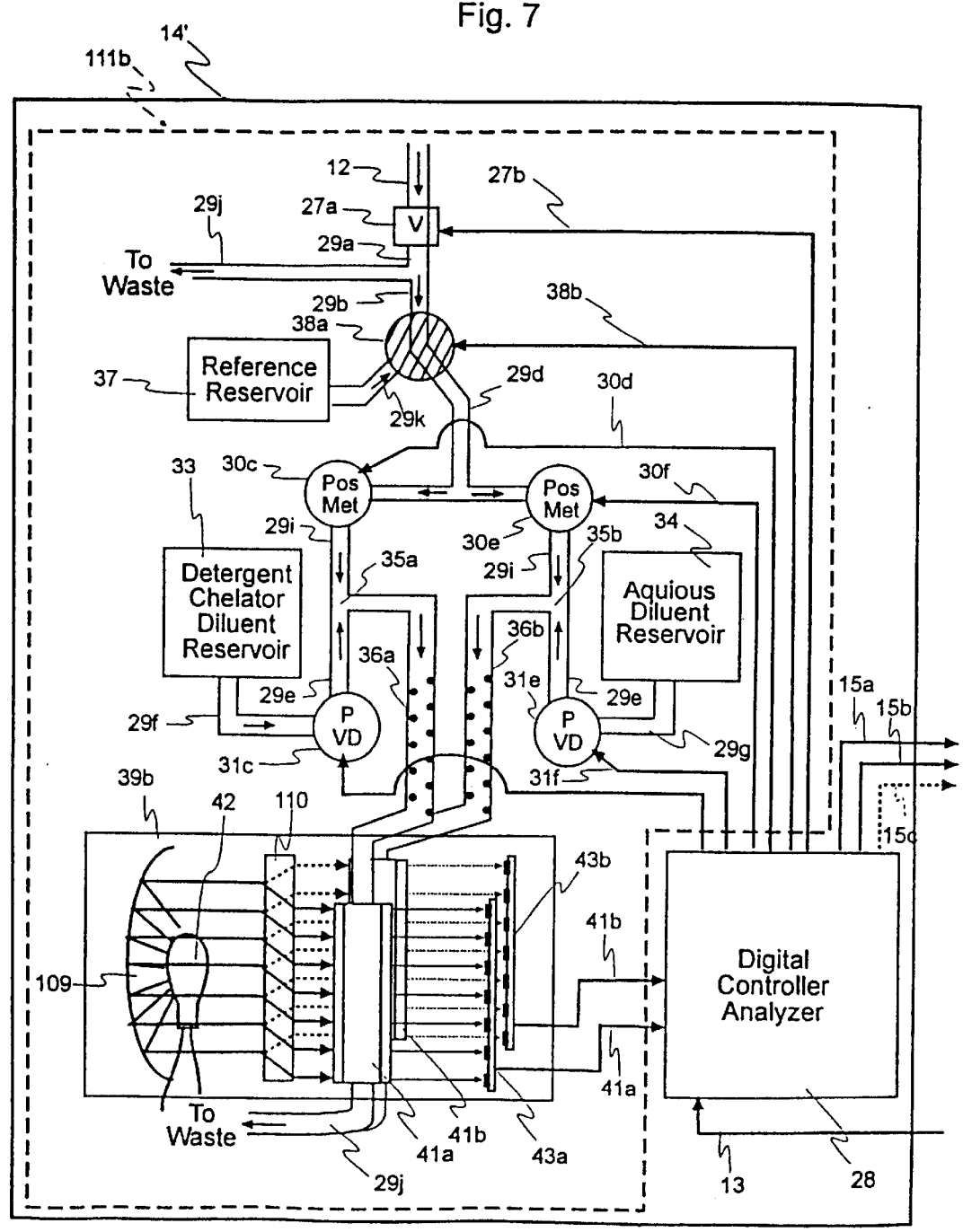
FIG. 7 is a schematic diagram illustration of a second embodiment of the present invention.

Referring to FIG. 7, spectrophotometer 39 of the first embodiment of digital controller testing device 14 (FIG. 4) is replaced with a dual beam spectrophotometer 39b of a second embodiment of digital controller testing device 14'. Consequently, digital controller testing device 14' simultaneously monitors both fat and fat plus micelle associated protein (MAP).

Sample milk is split as it leaves tube 29d and each portion enters its respective positive metering pump 30a and 30b. Each diluent, detergent chelating agent from reservoir 33 and aqueous diluent from reservoir 34, has a dedicated positive metering pump, pump 31c for detergent chelating diluent and pump 31e for aqueous diluent. Pump 31c meters the chelator detergent dilution of milk from pump 30c in mixing tube 36a. Pump 31e meters the water dilution of milk from pump 30e in mixing tube 36b. Since milk is split just before metered dilution the contents of mixing tubes 36a and 36b represent samples of equivalent composition taken at the same time in the same location in the flow. Mixing tube 36a delivers milk appropriately diluted with detergent chelator to a first flow cell cuvette 41a. Simultaneously, mixing tube 36b delivers milk appropriately diluted with aqueous diluent to a second flow cell cuvette 41b.

Light source 42 generates a beam of light 109 that is split by a splitter 110 and focused to pass through cuvettes 41a and 41b and strike photodetectors 43a and 43b. The presence of fat in cuvette 41a quantitatively in a concentration dependant manner absorbs some of the light from the split half of beam 109 that strikes photodetector 43a. This correlatively diminishes the analog signal sent from photodetector 43a down an absorbance output lead 40a to digital controller analyzer 28. Likewise, the presence of fat plus micelle associated proteins (MAP) in cuvette 41b quantitatively absorbs in a concentration dependant manner some of the light from the split half of beam 109 that strikes photodetector 43b. This correlatively diminishes the analog signal sent from photodetector 43b down absorbance output lead 40b to digital controller analyzer 28.

The fat content value of the entire analog signal from photodetector 43a is equal to the fat content value portion of the analog signal from photodetector 43b. Subtracting the value of the photodetector 43a signal from the value of the photodetector 43b signal gives the value of the MAP portion of the photodetector 43b signal. The subtraction can take place upon signal entry into digital controller analyzer 28 while the signals are in analog form or later after the signals are converted into digital information.

Using the second embodiment of digital controller testing device 14', the sample value for fat is compared with the standard value for fat at the same time that the sample value for MAP is compared with the standard value for MAP. Consequently cream screw 17b or 17c and skim screw 17a are adjusted simultaneously increasing the rapidity of response to fat and MAP concentration variations in the incoming raw milk and improving the reliability with which the desired finished product is obtained.

Referring now to Table I, a device of the present invention was used to obtain protein values on twenty reference samples of standardized milk from various production runs. Eleven samples were Holstein skim standardized with Holstein cream (sample code A), 5 samples were Holstein skim standardized with Jersey cream (sample code B), 5 samples were Jersey skim standardized with Jersey cream (sample code C), and 16 samples were Holstein skim standardized with

TABLE I

Protein Measurements on Standard Samples

| Sample | Standard | Expected | Measured | Residual |
|---|---|---|---|---|
| A | 3.31 | 3.32 | 3.32 | 0.00 |
| A | 3.31 | 3.32 | 3.34 |  |
| A | 3.24 | 3.25 | 3.21 | 0.04 |
| A | 3.29 | 3.30 | 3.35 | −0.05 |
| A | 3.28 | 3.29 | 3.36 | −0.07 |
| A | 3.28 | 3.29 | 3.36 | −0.07 |
| A | 3.25 | 3.26 | 3.23 | 0.03 |
| A | 3.24 | 3.25 | 3.21 | 0.03 |
| A | 3.25 | 3.26 | 3.23 | 0.02 |
| A | 3.21 | 3.22 | 3.18 | 0.04 |
| A | 3.21 | 3.22 | 3.23 | −0.01 |
| B | 3.47 | 3.47 | 3.39 | 0.09 |
| B | 3.46 | 3.46 | 3.37 | 0.09 |
| B | 3.59 | 3.59 | 3.46 | 0.13 |
| B | 3.60 | 3.60 | 3.47 | 0.13 |
| B | 3.60 | 3.59 | 3.49 | 0.11 |
| C | 4.16 | 4.14 | 4.17 | −0.03 |
| C | 4.16 | 4.15 | 4.18 | −0.03 |
| C | 4.17 | 4.15 | 4.14 | 0.02 |
| C | 4.15 | 4.13 | 4.18 | −0.04 |
| C | 4.16 | 4.14 | 4.11 | 0.03 |
| D | 3.32 | 3.32 | 3.32 | 0.00 |
| D | 3.43 | 3.43 | 3.48 | −0.05 |
| D | 3.54 | 3.54 | 3.60 | −0.06 |

TABLE I-continued

Protein Measurements on Standard Samples

| Sample | Standard | Expected | Measured | Residual |
|---|---|---|---|---|
| D | 3.63 | 3.63 | 3.64 | −0.01 |
| D | 3.85 | 3.84 | 3.82 | 0.02 |
| D | 3.29 | 3.30 | 3.31 | −0.01 |
| D | 3.47 | 3.56 | 3.47 | −0.09 |
| D | 3.57 | 3.57 | 3.57 | 0.00 |
| D | 3.56 | 3.56 | 3.66 | −0.10 |
| D | 3.86 | 3.85 | 3.88 | −0.03 |
| D | 3.29 | 3.30 | 3.29 | 0.01 |

Holstein cream and skim milk powder (sample code D). The reference values, provided with the standard samples and shown in column 2, ranged from 3.21 to 4.17. Based on these standard values an expected value was predicted (shown in column 3) using an algorithm (FIG. 6b). The actual value obtained by measuring the samples using the device of the present invention is shown in column 4, and the difference between the expected value and the measured value, called residual value is shown in column 5. With an n-value of 37 the standard deviation of the residuals was 0.055. The standard error of the expected values was 0.0567 with an R-squared value of 0.9657. The correlation of coefficient between the reference value and the measured value was 0.9667 with a standard error of the coefficient being 0.0308.

Having described preferred embodiments of the invention with reference to the accompanying drawings, it is to be understood that the invention is not limited to those precise embodiments, and that various changes and modifications may be effected therein by one skilled in the art without departing from the scope or spirit of the invention as defined in the appended claims.

What is claimed is:

1. A device for measuring fat and micellar associated protein (MAP) content in milk, comprising:
   a milk sampler, said milk sampler configured to utilize a method for measuring fat and MAP content in Milk comprising the step of splitting a sample of milk into first and second parts;
   a diluter flowably connected to said milk sampler, said diluter configured to utilize said method for measuring fat and MAP content in milk comprising the steps of diluting said first part with a detergent chelator, and diluting said second part with water; and
   an analyzer flowably connected to said diluter, said analyzer configured to utilize said method for measuring fat and MAP content in milk comprising the steps of measuring a fat based light absorbance of said first part, comparing said fat based light absorbance with a fat standard light absorbance, calculating a fat concentration of said sample, measuring a light absorbance of said second part, comparing said light absorbance of said second part with a fat-plus-MAP standard light absorbance, calculating a fat-plus-MAP concentration of said sample, and subtracting said fat concentration of said sample from said fat-plus-MAP concentration of said sample to obtain a MAP concentration.

2. The device of claim 1, wherein:
   said milk sampler is a tubing having a sampler inlet and a sampler outlet; and
   said sampler outlet is flowably connected to said diluter.

3. The device of claim 1, wherein said diluter includes:
   a first diluent reservoir having a first diluent outlet;

a second diluent reservoir having a second diluent outlet;

a means for selecting a diluent having first and second diluent inlets and a selected diluent outlet;

said first diluent inlet connected to said first diluent outlet;

said second diluent inlet connected to said second diluent outlet;

a means for diluting said sample having a selected diluent inlet, a sample inlet, and a diluted sample outlet;

said sampler outlet is flowably connected to said diluter at said sample inlet; and said selected diluent inlet is flowably connected to said selected diluent outlet.

4. The device of claim 3, wherein said means for diluting said sample includes:

a first positive metering pump flowably connected to said sample inlet;

a second positive metering pump flowably connected to said selected diluent outlet; and said first and second positive metering pumps flowably connected in common to said diluted sample outlet.

5. The device of claim 3, wherein said means for selecting includes a solenoid activated three-way gate valve.

6. The device of claim 3, wherein said means for selecting includes;

a first diluent positive metering pump having said first diluent inlet;

a second diluent positive metering pump having said second diluent inlet;

said first and second diluent positive metering pumps flowably connected to said selected diluent outlet; and electronic means for selecting an appropriate diluent.

7. The device of claim 1, wherein said analyzer is a spectrophotometer having a flow cell cuvette.

8. The device of claim 1, wherein said analyzer is a dual beam spectrophotometer having flow cell cuvettes.

* * * * *